United States Patent [19]

Erckel et al.

[11] 4,220,760
[45] Sep. 2, 1980

[54] DIAMINO-1,3,5-TRIAZINYLSTILBENE COMPOUNDS AND PROCESS FOR PREPARING SAME

[75] Inventors: Rüdiger Erckel, Eppstein; Erwin Schmidt, Kelkheim; Helmut Eckes, Frankfurt am Main; Güter Rösch, Bad Soden am Taunus, all of Fed. Rep. of Germany

[73] Assignee: Hoechst Aktiengesellschaft, Fed. Rep. of Germany

[21] Appl. No.: 959,521

[22] Filed: Nov. 13, 1978

[30] Foreign Application Priority Data

Nov. 16, 1977 [CH] Switzerland .................. 14005/77

[51] Int. Cl.² ..................................... C07D 463/10
[52] U.S. Cl. ............................. 542/460; 252/301.23
[58] Field of Search ................................. 542/460

[56] References Cited

U.S. PATENT DOCUMENTS

| | | | |
|---|---|---|---|
| 2,846,397 | 8/1958 | Ackerman | 542/460 |
| 3,817,991 | 6/1974 | Meyer et al. | 542/460 |

*Primary Examiner*—Arthur P. Demers
*Attorney, Agent, or Firm*—Connolly and Hutz

[57] ABSTRACT

Diamino-1,3-5-triazinylstilbene compounds of the formula

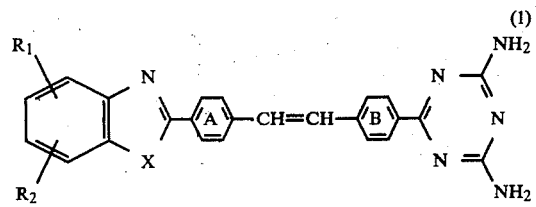

in which $R_1$ and $R_2$ may be identical or different and represent each hydrogen or non chromophoric radicals selected from the group consisting of fluorine or chlorine atoms, phenyl, alkyl, lower alkoxy, lower dialkylamino, lower trialkylammonium, acyl amino or optionally functionally modified carboxy or sulfo groups, or two vicinal radicals, $R_1$ and $R_2$ denote together lower alkylene, a fused benzo ring or 1,3-dioxypropylene, the rings A and B having optionally further non chromophoric substituents, and X is O or S.

These compounds are good optical brighteners and are prepared by reacting a 4'-cyano-4-benzoxazolyl- or 4'-cyano-4-benzthiazolylstilbene compound with dicyanoamide or with urea and ammonia.

4 Claims, No Drawings

DIAMINO-1,3,5-TRIAZINYLSTILBENE COMPOUNDS AND PROCESS FOR PREPARING SAME

The present invention relates to new diamino-1,3,5-triazinylstilbene compounds, to a process for preparing same and to their use as optical brighteners in organic materials. The new diamino-1,3,5-triazinylstilbene compounds correspond to the formula

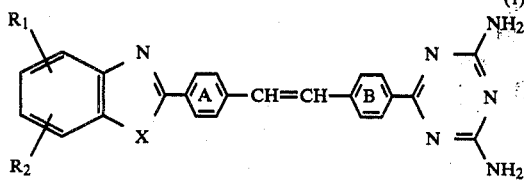

in which $R_1$ and $R_2$ may be identical or different and represent each hydrogen or non chromophoric radicals selected from the group consisting of fluorine or chlorine atoms, phenyl, alkyl, lower alkoxy, lower dialkylamino, lower trialkylammonium, acyl amino or optionally functionally modified carboxy or sulfo groups, or two vicinal radicals $R_1$ and $R_2$ denote together lower alkylene, a fused benzo ring or 1,3-dioxypropylene, the rings A and B having optionally further non chromophoric substituents, and X is O or S.

Non chromophoric substituents of the rings A and B are members of the group consisting of alkyl having from 1 to 12 carbon atoms, cyclohexyl, phenylalkyl having from 1 to 3 carbon atoms in the alkyl moiety, unsubstituted phenyl or phenyl substituted by 1 or 2 substituents selected from the group consisting of chlorine, methyl or methoxy, alkoxy having from 1 to 4 carbon atoms, unsubstituted phenoxy or phenoxy substituted by 2 substituents selected from the group consisting of chlorine, methyl or methoxy; chlorine, fluorine, bromine, cyano, —COOY with Y being hydrogen, a salt-forming cation, alkyl having from 1 to 5 carbon atoms or benzyl; CONY'(Y'$_1$) with Y' being hydrogen, alkyl having from 1 to 6 carbon atoms, hydroxyalkyl having from 1 to 4 carbon atoms, alkoxyalkyl having from 2 to 8 carbon atoms, phenyl or benzyl and with Y' being hydrogen, alkyl having from 1 to 6 carbon atoms, hydroxyalkyl having from 1 to 4 carbon atoms or alkoxyalkyl having from 2 to 8 carbon atoms or Y' and Y'$_1$ denoting together with the nitrogen atom a morpholine or piperidine radical, or modified sulfo groups such as —SO$_2$OY with Y having the aforesaid meaning, —SO$_2$NY'(Y'$_1$) with Y' and Y'$_1$ having the aforesaid meaning, alkylsulfonyl having from 1 to 6 carbon atoms, benzylsulfonyl or unsubstituted phenylsulfonyl or phenylsulfonyl substituted by chlorine or methyl, or, in the case of two substituents in ortho position alkyls having 3 or 4 carbon atoms, or 1,3-butadienylene.

Preference is given to compounds of the formula

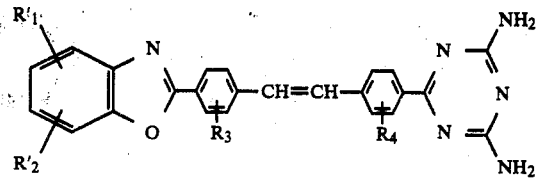

in which $R'_1$ and $R'_2$ independant from one another are hydrogen, fluorine, or chlorine atoms, phenyl, alkyl having from 1 to 9 carbon atoms, alkoxy having from 1 to 4 carbon atoms, carboxy, carbalkoxy having from 1 to 4 carbon atoms in the alkoxy moiety, cyano or modified sulfo groups or two vicinal radicals $R_1$ and $R_2$ denote together lower alkylene or a fused benzo ring and $R_3$ and $R_4$ independant from one another denoting a member of the group consisting of hydrogen, halogen, cyano, alkoxy having from 1 to 4 carbon atoms or modified sulfo groups above.

Compounds of the formula

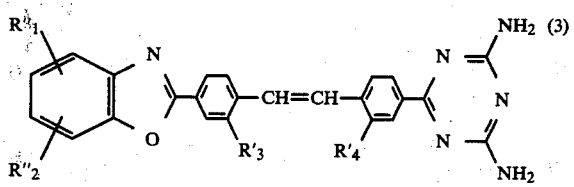

in which $R''_1$ and $R''_2$ independant from one another are hydrogen, fluorine or chlorine atoms, phenyl or alkyl having from 1 to 9 carbon atoms and $R'_3$ and $R'_4$ independant from one another are hydrogen, chlorine or cyano, are also preferred as well as compounds of the formula

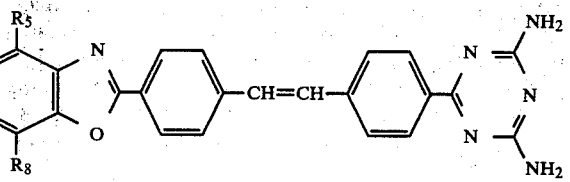

in which $R_5$, $R_6$, $R_7$ and $R_8$ each are hydrogen; $R_5$, $R_7$, $R_8$ each are hydrogen and $R_6$ is chlorine, $C_{1-4}$ alkyl or phenyl; $R_5$ and $R_7$ each are hydrogen and $R_6$ and $R_8$ each are $C_{1-4}$ alkyl or $R_5$ and $R_8$ each are hydrogen and $R_6$ and $R_7$ each are $C_{1-4}$ alkyl, are particularly preferred.

Compounds of the formulae

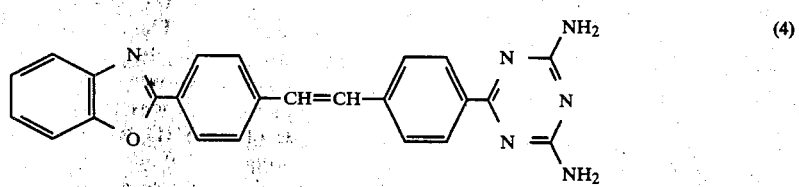

-continued

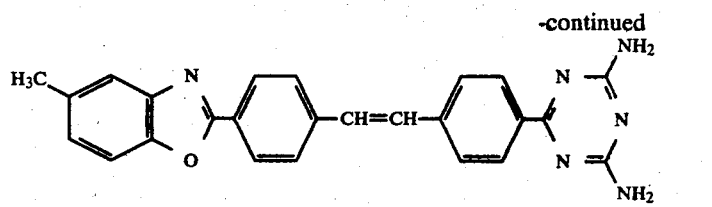 (5)

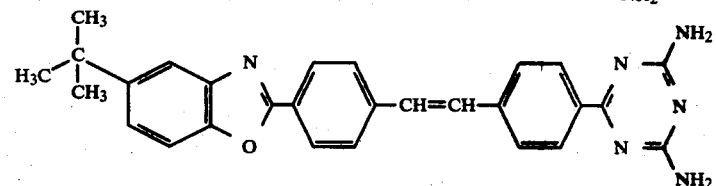 (6)

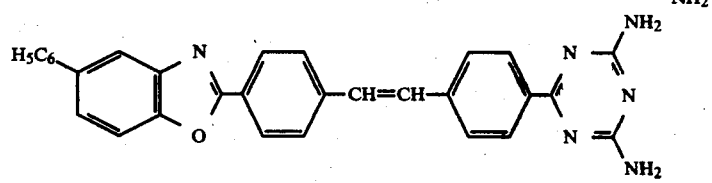 (7)

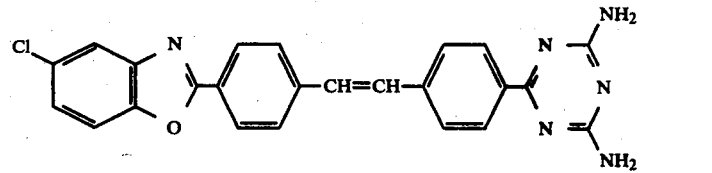 (8)

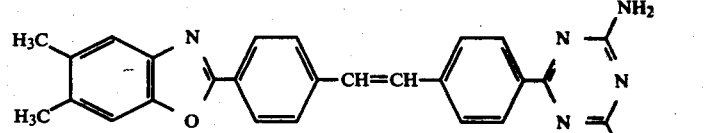 (9)

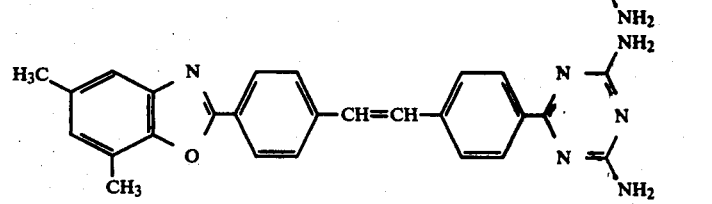 (10)

are particularly interesting.

"Functionally modified carboxy groups" are members of the group consisting of: cyano, carboxylic acid ester, carboxylic acid amide, mono- and dialkylcarbonamido groups. By the term "lower" there are to be understood groups having from 1 to 4 carbon atoms.

The diamino-1,3,5-triazinylstilbene compounds of the formula I are prepared in known manner according to Org. Synth. Coll. Vol. IV, 78 from derivatives of carboxylic acids

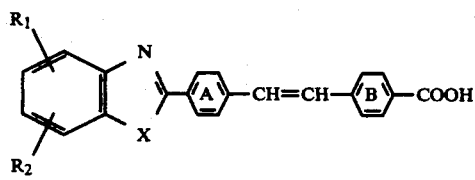 (13)

in which $R_1$, $R_2$, X, A and B have the aforesaid meaning, for example, from nitrile, by reaction with dicyanodiamide in the presence or in the absence of basic catalysts or from the corresponding amidine salt of the acid of the formula 13 by reaction with dicyanodiamide or biguanide salts or by reaction of the corresponding chloride of the acid of the formula 13 with biguanide salts or by reaction of the corresponding nitrile of the acid of the formula 13 with urea and ammonia.

A preferred mode of preparation consists in reacting the nitrile of the carboxylic acid (13) with dicyanodiamide with the addition of basic catalysts in the presence of polar solvents, at a temperature of from 70° to 250° C., optionally under pressure. Suitable solvents are, for example, methanol, ethanol, isopropanol, tertiary butanol, cyclohexanol, methyl glycol, methyl diglycol, butyl glycol, diglycol, dimethylformamide, phosphoric acid trisdimethylamide, dimethylsulfoxide, methylpyrrolidone.

Suitable basic catalysts include, for example, alkali metal carbonates, hydroxides, amides and alcoholates and primary, secondary and tertiary amines or quarternary ammonium bases. The alcoholates may alternatively be prepared by dissolving alkali metal, alkali metal amide or alkali metal hydride in the alcohol used as the solvent.

The carboxylic acids (13) used as the starting material or the corresponding nitriles and acid chlorides are known in the literature or may be prepared according to processes known in the literature (Japanese Patent JA-SHO No. 42-21013, U.S. Pat. No. 3,577,411, German Offenlegungsschrift No. 20 00 027). For example, the correspondingly substituted benzoxazolylstilbenecarboxylic acid can be converted into the amide according to processes known in the literature, by passing over the acid chloride and the amide may be converted into the corresponding nitrile according to processes known in the literature by reaction with a dehydrating agent.

A further possibility of preparing the compounds of the formula 2 consists in reacting a compound of the formula $$
\begin{array}{c}
H_2N \\
\phantom{H_2}\diagdown \\
N \phantom{xxx} N \\
\phantom{xx}\diagup \phantom{xxx}\diagdown \\
N \phantom{xxxxx} B \phantom{xx} Z_1 \\
\phantom{xx}\diagdown \phantom{xxx}\diagup \\
\phantom{H_2}\diagup N \\
H_2N
\end{array}
\quad (14)
$$

with a compound of the formula $$
\begin{array}{c}
R_1 \\
\phantom{R}\diagdown \\
\phantom{xxx} N \\
\phantom{xxxx}\diagdown \\
\phantom{xxxxx} B \phantom{xx} Z_2 \\
\phantom{xxxx}\diagup \\
\phantom{xxx} X \\
\phantom{R}\diagup \\
R_2
\end{array}
\quad (15)
$$

in which
$R_1$, $R_2$, X, A and B are defined as above and one of the symbols $Z_1$ and $Z_2$ is a —CHO— group and the other is a group of the formula $$
-CH_2-\overset{O}{\underset{\diagdown OD_1}{\overset{\|}{P}}}\!\!\diagup\!\!\overset{OD_1}{\phantom{x}} \quad -CH_2-\overset{O}{\underset{\diagdown D_1}{\overset{\|}{P}}}\!\!\diagup\!\!\overset{OD_1}{\phantom{x}}
$$

$$
-CH_2-\overset{O}{\underset{\diagdown D_1}{\overset{\|}{P}}}\!\!\diagup\!\!\overset{D_1}{\phantom{x}} \quad \text{or} \quad -CH=\overset{}{\underset{\diagdown D_1}{P}}\!\!\diagup\!\!\overset{D_1}{\phantom{x}}
$$

in which $D_1$ is unsubstituted or substituted alkyl, aryl, cyclohexyl or aralkyl.

These preparation processes are preferably performed in indifferent solvents, among which there may be mentioned, hydrocarbons such as toluene and xylene or alcohols such as methanol, ethanol, isopropanol, butanol, glycols, glycol ethers such as 2-methoxyethanol, hexanols, cyclohexanol and cyclooctanol, moreover ethers such as diisopropyl ethers, tetrahydofuran and dioxan or dimethylsulfoxide, formamide and N-methylpyrrolidone. Especially suitable are polar organic solvents such as dimethylformamide and dimethylsulfoxide. Some of the reactions may alternatively be performed in aqueous solution.

The reaction temperature may vary within wide limits.

It is determined (α) by the resistance of the solvent used to the reactants, in particular to highly basic alkali metal compounds,
(β) by the reactivity of the condensation partners and
(γ) by the efficiency of the combination solvent-base as condensation agent.

In practice temperatures of from 10° to 100° C. are generally chosen for the intended purpose, in particular when the solvent used is dimethylformamide or dimethylsulfoxide. The preferred temperature range is between 20° and 60° C.

As highly basic alkali metal compounds there may be mentioned in particular hydroxides, amides and alcoholates (preferably those of primary alcohols containing 1 to 4 carbon atoms) of the alkali metal, alkali metal compounds of lithium, sodium and potassium being of particular interest for economical reasons. On principle and in particular cases alkali metal sulfides and carbonates, aryl alkali metal compounds such as phenyl-lithium or highly basic amines, inclusive of ammonium bases, such as trialkylammonium hydroxides, may be used alternatively.

The compounds of the formula $$
\begin{array}{c}
R_5 \phantom{xxxxxxxxxxxxxxxxxxxxxxxxxx} NH_2 \\
R_6 \diagdown \phantom{xx} \diagup N \diagdown \phantom{xxxxxxxxxxx} \diagup N \diagdown \\
\phantom{xxxxx} \phantom{xx} \phantom{xxxx}\diagdown CH=CH \diagup \phantom{xxxx} N \\
R_7 \diagup \phantom{xx} \diagdown X \diagup \phantom{xxxxxxxxxxx} \diagdown N \diagup \\
R_8 \phantom{xxxxxxxxxxxxxxxxxxxxxxxxxx} NH_2
\end{array}
\quad (16)
$$

in which X is O or S,
$R_5$, $R_6$, $R_7$, $R_8$ each are hydrogen or halogen,
$R_5$ and $R_6$ or $R_6$ and $R_7$ denote together a fused benzo ring and
$R_6$ and $R_8$ each are alkyl having from 1 to 8 carbon atoms,
may be prepared by reacting a Schiff's base of the formula $$
\begin{array}{c}
R_5 \\
R_6 \diagdown \phantom{xx} \diagup N \diagdown \phantom{xxxxxxxx} \\
\phantom{xxxxxx} \phantom{xxxx}\diagdown CH=N \diagup \phantom{xx} \diagdown Y \\
R_7 \diagup \phantom{xx} \diagdown X \diagup \\
R_8
\end{array}
\quad (17)
$$

in which $R_5$, $R_6$, $R_7$, $R_8$ and X are defined as above and Y is hydrogen or chlorine, in a polar, neutral to basic solvent in the presence of a highly basic alkali metal compound, with a methyl compound of the formula $$
\begin{array}{c}
H_2N \\
\phantom{H_2}\diagdown \\
\phantom{xx} N \\
\phantom{xxx}\diagdown \\
N \phantom{xxxxx} \diagup \phantom{xx}\diagdown \\
\phantom{xxx}\diagup \phantom{xxxx} CH_3 \\
\phantom{xx} N \\
\phantom{H_2}\diagup \\
H_2N
\end{array}
\quad (18)
$$

Alternatively, compounds of the formula (16) may be prepared by reacting a methyl compound of the formula

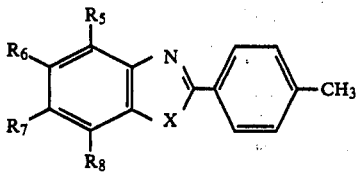

with a Schiff's base of the formula

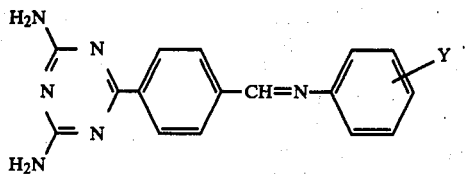

in which $R_5$, $R_6$, $R_7$, $R_8$, S and Y are defined as above.

The methylene group-containing compounds can be reacted with the anils in the presence of a suitable highly polar, neutral to alkaline organic solvent which is free from those atoms, in particular hydrogen atoms, which may be replaced by alkali metals. In practice suitable solvents of this type include in particular dialkylamides of formic acid and of phosphoric acid as well as tetraalkylureas, "alkyl" denoting lower alkyl having from 1 to 4 carbon atoms, in particular methyl. As most important representatives of these solvents there may be mentioned: diethylformamide, hexamethylphosphoric acid triamide, tetramethyl-urea and in particular dimethylformamide. Mixtures of solvents may alternatively be used.

As mentioned above, a highly basic alkali metal compound is required for the reaction according to the invention. These compounds depend on the nature of the solvent used and on the reactivity of the anil used and may be specific sodium alcoholates such as sodium t-butylate and in particular potassium compounds of the formula $$KOC_{m-1}H_{2m-1}$$

in which m is an integer from 1 to 6, preferably from 2 to 6, such as potassium hydroxide or in particular potassium tertiary butylate.

In the case of alkali metal alcoholates a practically anhydrous medium should be used, whereas in the case of potassium hydroxide a low water content up to about 15% (for example crystal water content) is still permissible. In some cases potassium hydroxide or sodium t-butylate is combined preferably with hexamethylphosphoric acid triamide at elevated temperature, for example from 100° to 130° C. It is quite natural that mixtures of different bases may be used alternatively.

The methyl group-containing compounds may be reacted with anils in equivalent quantities, i.e. in a molar ratio of 1:1. In general an excess of anil of up to about 50% is advantageous. The alkali metal compound is generally used in at least the equivalent quantity, i.e. at least one mol of a compound containing for example a KO group for one mol of aldehydanil. When using potassium hydroxide, the 4- to 8-fold quantity is employed in general.

Especially good yields are obtained when using potassium t-butylate in the 1- to 6-fold, preferably the 2- to 4-fold equivalent quantity.

The reaction according to the invention can be performed generally at a temperature in the range of from about 10° to 150° C. In the case of particularly reactive anils, the reaction is successful at room temperature and requires no external heat supply. This procedure is advantageous when the reactants contain ring compounds or substituents that can be readily opened or split off by alkalis or can be chemically modified in another way. This applies for example to anils containing chlorine substituents that may be readily splitt off. The process of the invention is carried out most advantageously at elevated temperature. For example, the reaction mixture may be slowly heated to 30° to 80° C. and be kept at this temperature for some time, for example for half an hour to 2 hours. The preparation of the anil and the reaction of anil with the tolyl compound may alternatively be carried out in a one-pot process. For example, the aldehyd may be heated with excess anilin in dimethylformamide, the solvent is evaporated completely in vacuo, the tolyl component and dimethylformamide are added, and the rest of the procedure is as that known to the expert. The final products may be worked up from the reaction mixture by usual methods. They may be isolated, for example by precipitation with water, in the case of water-soluble products by salting-out, for example using NaCl, KCl or by neutralisation, optionally by acidification with a strong mineral acid such as HCl, in the latter cases the free sulfonic acid may be optionally precipitated. They may be converted into the corresponding alkali metal, alkaline earth metal, ammonium or amine salts by reacting them with alkali metal or alkaline earth metal salts or with ammonium hydroxide or amines. It may be advisable to initiate the reaction by radiation with ultraviolet light above 300 nm. The starting products for the manufacture of the compounds of the formulae 1 to 13 and 16 are known or may be prepared in accordance with known processes. Alternatively, the compounds of the formula (13) may be prepared by converting stilbene compounds prepared according to methods known per se and being substituted in 4-position by cyano and in 4'-position by an optionally modified carboxyl group such as the acid chloride, to yield the corresponding benzoxyzolyl compounds.

The new compounds defined as above exhibit a more or less pronounced fluorescence in dissolved or finely dispersed state. They may be used for the optical brightening of a great variety of synthetic, semi-synthetic or natural organic materials or substances, which contain these organic materials.

Hereinafter there are listed, by way of example only, groups of organic materials which can be optically brightened:

I. Synthetic Organic High Molecular Materials (a) Polymerization products based on organic compounds containing at least one polymerizable hydrocarbon-hydrocarbon double bond, i.e. homo- and copolymers thereof and aftertreatment products thereof such as cross-linked products, graft products or decomposition products, mixtures of polymers or products obtained by modification or reactive groups, for example polymers based on α,β-unsaturated carboxylic acids or on derivatives of these acids, in particular of acrylic compounds such as acrylic esters, acrylic acid, acrylonitrile, acrylamides and derivatives thereof or methacrylic analogous compounds thereof; on olefin-hydrocarbons such as ethylene, propylene, styrenes or dienes, or so-called ABS-polymers; polymers based on vinyl and vinylidene compounds such as vinyl chloride, vinyl alcohol, vinylidene chloride.

(b) Polymerization products obtainable by cyclization, for example polyamides of the polycaprolactam type, or polymers obtainable both by polyaddition or by polycondensation such as polyethers or polyacetals.

(c) Polycondensation products or precondensates based on bi- or polyfunctional compounds containing groups that are capable of being condensed, homo- and cocondensation products thereof or products obtained in the aftertreatment such as polyesters, in particular saturated, for example ethylene glycol terephthalic acid polyester, or unsaturated, for example maleic acid dialcohol polycondensates or cross-linked products thereof having vinyl monomers that may be added by polymerization, unbranched or branched polyesters, those based on polyvalent alcohols such as alkyl resins, included, polymides, for example hexamethylene diamine-adipate, maleinate resins, precondensates and analogous compounds thereof, polycarbonates, silicones.

(d) Polyaddition products such as polyurethan, which may be cross-linked or non-cross-linked, epoxyde resins.

II. Semi-synthetic organic materials, for example cellulose esters having various esterification degrees (the so-called 2½ acetate, triacetate) or cellulose ethers, regenerated cellulose (viscose, copper ammonia cellulose) or aftertreatment products thereof, casein plastics.

III. Natural organic materials stemming from animals or from plants, for example based on cellulose or proteins such as cotton, wool, linen, silks, natural lacquer resins, starch, casein.

The organic materials to be optically brightened may be present in various states of processing, for example as crude products, semi-finished or finished products. They may moreover have a great variety of shapes, i.e. mainly three-dimensional bodies such as plates, profiles, injection molded articles, chips, granules, or foams, mainly two-dimensional bodies such as sheets, foils, lacquers, coatings, impregnations or mainly one-dimensional bodies such as threads, fibers, flocks, wires. Said materials may alternatively be present in a non-shaped state in various homogeneous or inhomogeneous distribution states, for example as powders, solutions, emulsions, dispersions, latices, pastes or waxes.

Fiber materials may be present as continuous filaments, stretched or unstretched, staple fibers, flocks, material in rope form, textile threads, yarns, twisted yarns, non-wovens, felts, laps, flocked articles or as textile fabrics or textile sandwiching-material, knit fabrics or papers, card-boards or paper pastes.

The compounds to be used according to the invention are inter alia important for the treatment of textile organic materials, in particulr textile fabrics. Fibers present as staple fibers or as continuous filaments in the form of ropes, fabrics, knit fabrics, non-wovens, flocked substrates or sandwiching material are advantageously optically brightened in aqueous medium containing the corresponding compounds in finely distributed form, as suspensions, so-called microdispersions, optionally solutions. Dispersion agents, stabilizers, cross-linking agents and further auxiliaries may be added in the treatment.

In dependence on the type of brightener used it may be advantageous to operate in a neutral, alkaline or acid bath. The treatment is generally performed at a temperature of from about 20° to 140° C., for example at the boiling temperature of the bath or near the boiling temperature, at about 90° C. Solvents may also be used for the finishing of textile substrates according to the invention, as is customary in dyeing practice in so-called solvent dyeing (padding-thermofixation application, exhaustion process in dyeing machines).

The new optical brighteners according to the present invention may be added to the material prior to or during moulding. In the manufacture of sheets or foils, for example, they may be incorporated in polyvinyl chloride by rolling at elevated temperature or in the manufacture of shaped articles they may be added to the molding or to the injection molding compositions.

When fully synthetic or semi-synthetic organic materials are shaped by spinning processes or by means of spinning pastes, the optical brighteners may be applied according to the following methods:

addition to the starting substances, for example monomers, or to intermediates, for example precondensates, prepolymers, i.e. prior to or during polymerization, polycondensation or polyaddition, dusting onto polymerization chips or granules for spinning pastes, bath dyeing of polymerization chips or granules for spinning pastes, proportioned addition to spinning melts or spinning solutions, application onto tows prior to stretching.

The new optical brighteners according to the invention may be used in the following forms, for example:

(a) As mixtures with dyestuffs (tinting) or pigments (color pigments or in particular white pigments) or as addition to dyebaths, printing pastes, discharge or resist pastes. Moreover for the aftertreatment of colorations, prints or discharge prints, (b) in admixture with so-called "carriers", wetting agents, softeners, swelling agents, antioxidants, light and heat stabilizers, chemical bleaching agents (sodium chlorite bleaching, additives to bleaching baths), (c) in admixture with cross-linking agents or finishing agents, for example starch or synthetic finishing agents, or in combination with a great variety of textile finishing agents, in particular artificial resin finishes, for example, crease-resistant finishes such as "wash-and-wear", "permanent-press", "no-iron", or flame-proof finishes, soft handle, anti-soiling, anti-static or anti-microbial finishes, (d) incorporation of the optical brighteners in polymer carrier materials for example polymerization, polycondensation or polyaddition products, in dissolved or dispersed form for use in coating agents, impregnation agents or adhesives, for example as solutions, dispersions, emulsions, for textiles, nonwovens, paper, leather, (e) as additives to so-called "master batches", (f) as additives to a great variety of industrial products to bring them in a form that it easier marketable (for example for improvements of the appearance of soaps, detergents, pigments), (g) in combination with other optically brightening substances, (h) in spinning bath compositions, i.e. additives to spinning baths used for improving the lubricating properties for the processing of synthetic fibers, or in a special bath prior to stretching of the fiber, (i) as scintillators for various purposes in the photographic field, for example for electrophotographic reproduction or supersensibilization, (j) in dependence on the substituents as laser dyestuffs.

When the brightening process is combined with textile treatment or finishing methods, corresponding resistant compositions are used advantageously that contain the optically brightening compounds in a concentration sufficient to obtain the desired brightening effect.

In some cases the action of the brighteners may be improved by an after-treatment, for example a chemical acid treatment, a thermal treatment or a combined chemical/thermal treatment. Hence, when optically brightening a number of fiber substrates, for example polyester fibers, with the brighteners according to the invention, these fibers are advantageously impregnated with aqueous dispersions, optionally solutions, of the brighteners, at a temperature below 75° C., for example at room temperature, and subsequently submitted to a dry heat treatment, at a temperature above 100° C., these steps being advantageously preceeded by drying the fibrous material at moderately elevated temperature, for example of at least 60° C. up to about 130° C. In this case the heat treatment in the dry state is advantageously carried out at a temperature between 120° and 225° C., by ironing with dry, superheated steam. Drying and the dry heat treatment may follow each other immediately or by combined in a single step.

The quantity of the new optical brighteners according to the invention, calculated on the material to be brightened optically, may vary within wide limits. A distinct and durable effect may be achieved with very small quantities, in some cases even with those below 0.001 weight %. Quantities up to about 0.8 weight % and optionally up to about 2 weight % may be used alternatively, quantities between 0.005 and 2, preferably between 0.1 and 0.5 weight % being interesting for most practical purposes.

For various reasons the brighteners should frequently be used not as such, i.e. in the pure state, but in admixture with various auxiliaries such as anhydrous sodium sulfate, sodium sulfate decahydrate, sodium chloride, sodium carbonate, alkali metal phosphates, such as sodium or potassium orthophosphate, sodium or potassium pyrophosphate and sodium or potassium triphosphates, or alkali metal silicates.

The new optical brighteners are especially suitable as additives to washing baths or to industrial and household washing agents. They are suitably added to washing baths in the form of their solutions in water or in organic solvents or in finely divided state as aqueous dispersions. To household or industrial washing agents they are suitably added in whatever phase of the manufacture process, for exmaple to the so-called "slurry" prior to atomization or they are added during the manufacture of liquid combinations of washing agents. They may be added either as solution or as dispersion in water or in another solvent or without auxiliaries as dry brightening powder. The brighteners may be mixed, kneaded or ground with the active detergents and be added in this form to the finished washing powder. Alternatively, they may be sprayed onto the ready washing powder in dissolved or in predispersed state.

Suitable washing agents are the known mixtures of active detergents such as soap in the form of chips and powder, synthetics, soluble salts of sulfonic acid semiesters of higher fatty alcohols, of higher and/or multiple alkyl-substituted arylsulfonic acids, sulfocarboxylic acid esters of medium to higher alcohols, fatty acid acyl-aminoalkyl- or -aminoacrylglycerol sulfonates, phosporic acids esters of fatty alcohols etc. Suitable "builders" are in particular alkali metal poly- and -polymetaphosphates, alkali metal pyrophosphates, alkali metal salts of carboxymethylcellulose and other soil-redeposition inhibitors, further alkali metal silicates, alkali metal carbonates, alkali metal borates, alkali metal perborates, nitrilotriacetic acid, ethylene diamino-tetraacetic acid, foam stabilizers such as alkanolamides of higher fatty acids. The washing agents may further contain antistatic agents, refattening skin-protective agents such as lanolin, enzyms, antimicrobials, perfums and colorants.

A particular advantage of the new optical brighteners resides in the fact that they are efficient even in the presence of active chlorine donators such as hypochloride, and that they can be used with nearly the same good efficiency in washing baths containing non-ionogenic washing agents such as alkylphenolpolyglycol ethers.

The compounds according to the invention are used in an amount from 0.005 to 1% or more, calculated on the weight of the liquid or powdery ready washing agent. When textiles made from cellulose fibers, polyamide fibers, highly finished cellulose fibers, polyester fibers, wool etc. are washed with washing liquor which contain the above-indicated quantities of the claimed optical brighteners, they exhibit a brillant aspect when exposed to daylight.

The washing treatment is carried out as follows: The textiles are washed for 1 to 30 minutes, at a temperature of from 20° to 100° C. in a washing bath containing up to 10 g/kg of a washing agent and from 0.05 to 1%, calculated on the weight of the washing agent, of the claimed brighteners. The goods-to-liquor ratio may be from 1:3 to 1:50. After washing, the textiles are rinsed and dried in usual manner. The washing bath may contain as bleaching additive 0.2 g/l of active chlorine such as hypochloride or from 0.1 to 2 g/l of sodium perborate.

Compounds of the formula (1) in which $R_3$ and/or $R_4$ denote modified sulfo groups, are especially appropriate for brightening cotton and polyamides.

The following examples illustrate the invention. Percentages are by weight unless otherwise stated. The melting and boiling points are uncorrected.

EXAMPLE 1a 171 g 4'-benzoxazolyl-2-stilbenecarboxylic acid are refluxed in 1500 ml toluene with 428 g thionyl chloride and 1 g dimethylformamide for 5 hours. The excess thionyl chloride is distilled off with toluene, the contents of the flask are cooled to 30° C. and ammonia is introduced until saturation is attained. Refluxing is continued for 2 hours while further introducing ammonia. After cooling, the resulting product is suction-filtered, washed and dried.

146 g (86% of the theory) of 4'-benzoxazolyl-2-stilbenecarboxylic acid amide of the formula

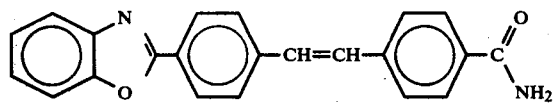

are obtained, which are refluxed subsequently for 6 hours without further purification in a mixture of 1400 g thionyl chloride and 5 g DMF. The thionyl chloride is distilled off to dryness, the residue is stirred with water, suction-filtered, washed neutral and dried. 131 g (95% of the theory) of 4'-benzoxazolyl-2-stilbenecarboxylic acid nitrile of the formula

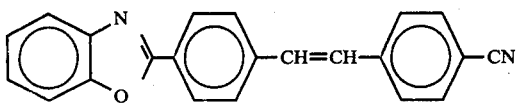

are obtained which melt after recrystallization from methylglycol with animal charcoal at 240° to 242° C.
IR: C≡N 2222 cm$^{-1}$
UV: $\lambda_{max}=358$ nm $\epsilon=7,7\times 10^4$ (in DMF) fluorescence (in DMF): $\lambda_{max}=414$ nm

EXAMPLE 1b 32.2 g (0.1 mol) 4'-benzoxazolyl-2-stilbene-4-carboxylic acid nitrile are refluxed while stirring in 1000 ml methylglycol with 9.3 g dicyano-diamide and 2.0 g powdered potassium hydroxide for 8 hours. Thereafter the resulting product is suction-filtered at room temperature, washed neutral with methanol and with water subsequently. 35 g (86.1% of the theory) of the compound of the formula

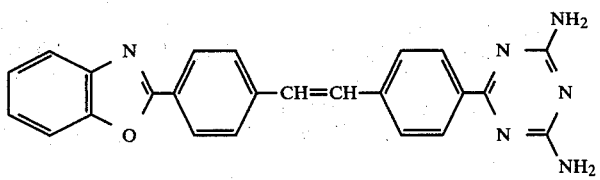

are obtained in the form of a light yellow powder having a melting point above 340° C.
Analysis: C$_{24}$H$_{18}$N$_6$O [406.4]—calc. C70.92, H4.46, N20.68; found C71.1, H4.6, N20.4.
UV (measured in dimethylformamide) $\lambda_{max}=364$ nm $\epsilon=7.13\times 10^4$.
fluorescence (in DMF): 420 nm.

EXAMPLE 2a 454.6 g (3 mols) p-cyanobenzyl chloride and 560.0 ml (3.3 mols) triethyl phosphite are heated for 5 hours to 140 to 145° C. p-Cyano-benzylphosphonic acid diethyl ester is obtained in an Arbusow reaction while ethyl chloride is split off. The reaction mixture is cooled to room temperature, a high vacuum is applied and the mixture is slowly heated to an inner temperature of about 100° C. to distill off the excess triethyl phosphite. The crude phosphonic acid ester can be used for the following reaction without further purification.
Yield: 751.5 g (99%) purity (GC): 96.1%

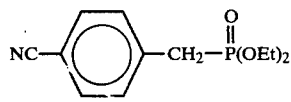

EXAMPLE 2b 112.2 g KOH powder (2 mols) are suspended in 1 liter DMF in a nitrogen atmosphere. A solution of 128 g phosphonic acid of Example 2a and 75 g p-carboxybenzaldehyde (0.5 mol) in 1 liter DMF is added dropwise while cooling with ice water in a way that the inner temperature does not ascend above 25° C. and the mixture is stirred for 12 hours at room temperature. The reaction mixture is poured into 5 liters ice water which has been acidified with 200 ml concentrated HCl, the suspension is briefly heated to 90° C., the crystal slurry is suction-filtered after cooling, washed neutral with water and dried. 105.5 g (85.9%) 4-cyanostilbenecarboxylic acid-(4') of the formula

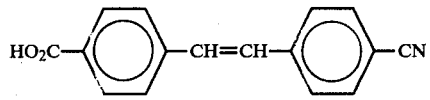

is obtained having a melting point of from 296° to 300° C. which after recrystallization from benzoic acid methyl ester with clarification with animal charcoal melts at a temperature from 301° to 302° C.

EXAMPLE 2c 24.9 g (0.1 mol) 4-cyano-stilbenecarboxylic acid-(4') are heated for 2 hours to 70° to 100° C. in 250 ml chlorobenzene with 9.2 ml (0.11 mol) thionyl chloride. Thereafter the excess thionyl chloride is distilled off, 18.5 g (0.1 mol) 4-phenyl-2-aminophenol and 12.1 g (0.1 mol) N,N-dimethylaniline are added and the mixture is refluxed for 45 minutes. Thereafter it is cooled, suction-filtered, washed with ethanol and dried. 36.5 g (90%) of crude acylic compound having a melting point of from 262° to 264° C. are obtained, which is heated to 212° C. in 600 ml trichlorobenzene for 2 hours after having added a little p-toluene-sulfo acid, thereafter suction-filtered at room temperature, washed with ethanol and dried. 34.4 g (96.1%) 4-[5-phenyl-benzoxazolyl-(2)]-4'-cyanostilbene of the formula

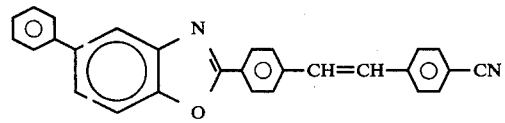

are obtained having a melting point (liquid-crystalline transition) from 237° to 239° C. and after recrystallization from dimethylformamide with clarification with animal charcoal from 240° to 242° C., clarification point 360° C.
Analysis: C$_{28}$H$_{18}$N$_2$O [455.5]—calc. C 84.5, H 4.6, N 7.05; found C 84.2, H 4.6, N 6.9.
UV (measured in dimethylformamide); $\lambda_{max}=362$ nm; $\epsilon=7.17\times 10^4$.
fluorescence (in DMF): 422 nm.

EXAMPLE 2

45.6 g (0.1 mol) 4'-[5-phenyl-benzoxazolyl-2]-stilbene-4-carboxylic acid nitrile are refluxed while stirring in 600 ml methyldiglycol with 9.3 dicyanodiamide and 2.0 g powdered potassium hydroxide for 8 hours. Thereafter the resulting product is suction-filtered at room temperature, washed neutral successively with methanol and with water and dried. 39 g (81%) of the compound of the formula

[chemical structure]

are obtained in the form of a light yellow powder having a melting point above 340° C.

Analysis: $C_{30}H_{22}N_6O$ [482.6]—calc. C 74.67, H 4.60, N 17.52; found C 74.80, H 4.70, N 17.20.

UV (measured in dimethylformamide); $\lambda_{max}=368$ nm; $\epsilon=81700$.

fluorescence (in DMF): $\lambda_{max}=427$ nm.

EXAMPLE 3a

When operating as in Example 2c, but using instead of 4-phenyl-2-aminophenol 12.3 g (0.1 mol) of 2-amino-p-kresol, there are obtained 28.3 g (84% of the theory) of the compound of the formula

[chemical structure]

which after two recrystallizations from o-dichlorobenzene and clarification with animal charcoal exhibits a liquid-crystalline transition of from 235° to 237° C. Clarification point 300° C.

Analysis: $C_{23}H_{16}N_2O$ [336.4]—calc. C 82.5, H 4.76, N 8.32; found C 81.80, H 4.90, N 8.1.

UV (measured in dimethylformamide); $\lambda_{max}=360$ nm; $\epsilon=6.95\times10^4$.

fluorescence (in DMF): $\lambda_{max}=420$ nm.

EXAMPLE 3b

When reacting the nitrile obtained in Example 3a analogously to Example 1b, there are obtained 35.1 g (85% of the theory) of the compound of the formula

[chemical structure]

which after recrystallization from dimethylformamide with clarification with animal charcoal melts at a temperature above 340° C.

Analysis: $C_{25}H_{20}N_6O$ [420.5]—calc. C 71.40, H 4.79, N 19.98; found C 71.1, H 5.0, N 19.5.

UV (in DMF): $\lambda_{max}=366$ nm; $\epsilon=7.43\times10^4$.
fluorescence (in DMF): 428 nm.

EXAMPLE 4a

When operating as in Example 2c, but using instead of 4-phenyl-2-aminophenol 13.7 g of 4,5-dimethyl-2-aminophenol, there are obtained 28.2 g (81% of the theory) of the compound of the formula

[chemical structure]

which after recrystallization from benzoic acid methyl ester with clarification with animal charcoal exhibits a liquid-crystalline transition of from 263° to 265° C. and has a clarification point of 302° C.

UV (measured in DMF); $\lambda_{max}=366$ nm; $\epsilon=6.46\times10^4$.

EXAMPLE 4b

When reacting the nitrile obtained in Example 3a analogously to Example 1b, there are obtained 34 g (79% of the theory) of the compound of the formula

[chemical structure]

having a melting point of 300° C.
UV (in DMF): $\lambda_{max}=360$ nm.
fluorescence (in DMF): $\lambda_{max}=428$ nm.

EXAMPLE 5

4.02 g (0.02 mol) 2,4-diamino-6-p-tolyl-1,3,5-triazine of the formula (melting point 245° C.)

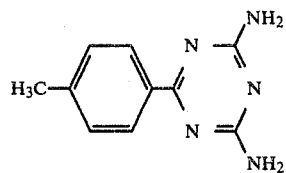

and 6.87 g (0.02 mol of the Schiff's base of 2-(p-formyl-phenyl)-benzoxazole of the formula

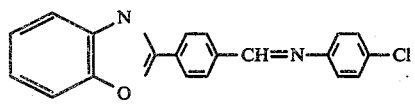

and 8.8 g of potassium-t-butylate are stirred under nitrogen in 200 ml of DMF for 1 hour at 25° to 35° C. During the first 15 minutes of the reaction the reaction mixture is exposed to UV-radiation of a wave length above 300 nm. Thereafter 800 ml of methanol are added to the violet suspension and the precipitated product is suction-filtered at 0° C., washed successively with methanol and with water. The crude product is stirred in 100 ml of water and its pH is adjusted to 6–8 with acetic acid, the resulting product is again suction-filtered, washed with water and dried.

After two recrystallizations from DMF with clarification with animal charcoal there are obtained 3.9 g (47.6% of the theory) of a compound as described in Example 1b.

The following compounds are obtained analogously to Example 1b and 2c:

| Compounds | Fp (°C.) | Absorption (in DMF) max (nm) | | fluorescence (in DMF) max (nm) |
|---|---|---|---|---|
| 6a | 252–255 | — | — | — |
| 6b | >300 | 368 | $6.05 \times 10^4$ | 427 |
| 7a | 249–251 | 360 | $6.18 \times 10^4$ | 430 |
| 7b | 317–318 | 366 | $7.43 \times 10^4$ | 423 |
| 8a | 236–238 | 360 | $6.59 \times 10^4$ | 420 |
| 8b | >300 | 366 | $7.35 \times 10^4$ | 422 |
| 9a | 108–110 | 361 | $55.31 \times 10^4$ | 422 |
| 9b | 262 | 367 | $7.64 \times 10^4$ | 423 |

| Compounds | Fp (°C.) | Absorption (in DMF) max (nm) | | fluorescence (in DMF) max (nm) |
|---|---|---|---|---|
| 10a | 201–204 | 360 | 6.66 × 10⁴ | 424 |
| 10b | | | | |
| 11a | 252–255 | 358 | 6.89 × 10⁴ | 412 |
| 11b | | | | |

For applying the compound of the invention on textile material, each time 100 mg of the compound of Example 1b (100%) are dissolved in 10 ml DMF at elevated temperature and admixed with 5 ml of an emulsifier. The resulting clear solution is poured while stirring into 85 ml of an aqueous solution containing 100 ml/l of the same emulsifier. A stable dispersion is obtained which contains 1 g/l of the optical brightener.

APPLICATION EXAMPLE 1

A fabric made from polyester fibers is impregnated with the above described dispersion and subsequently squeezed between two rubber rolls to a residual humidity of about 70%. Thereafter it is placed on a tenter frame and exposed to a temperature of 190° C. for 30 seconds to dry the tissu and to fix the brightener thereon. The fabric exhibits thereafter a very high degree of whiteness, which is distinctly higher than that of an untreated fabric.

APPLICATION EXAMPLE 2

A polyamide fabric is impregnated with a liquor containing the above described dispersion in an amount corresponding to 0.1% of the weight of the fabric and 1 g/l of bleaching agent, at 98° C. for 1 hour with a goods-to-liquor ratio of 1:15. Thereafter the fabric is rinsed and dried. It has a very high degree of whiteness, which is distinctly higher than that of an untreated fabric.

APPLICATION EXAMPLE 3

A solution of the brightener of Example 1b in DMF is prepared. The brightener solution is added to a spinning solution of polyacrylonitrile in DMF in an amount of 200 ppm, calculated on polyacrylonitrile. The spinning mass is pressed through spinnerets and the solvent is evaporated in the dry heat while taking-up the filaments. After stretching, the fiber exhibits a brilliant white shade, which is distinctly higher than that of filaments containing no brightener.

APPLICATION EXAMPLE 4

Brightener substrate is sprayed onto polyester granules placed in a mixer in an amount of 200 ppm, calculated on PES. Injection molded parts are manufactured from these granules on an injection molding machine, at a temperature of 260° C. These molded pieces exhibit an excellent degree of whiteness of high light resistance.

What is claimed is:

1. Diamino-1,3,5-triazinylstilbene compounds of the formula

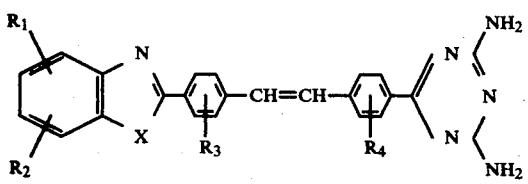

in which $R_1$ and $R_2$ may be identical or different and are each hydrogen, fluorine, chlorine, phenyl, alkyl, lower alkoxy, lower dialkylamino, lower trialkylammonium, acylamino, carboxy, cyano, carboxylic acid ester, carbonamido, nono- or dialkylcarbonamido, sulfo, sulfonic acid ester, sulfonamido, mono- or dialkylsulfonamido or two vicinal radicals $R_1$ and $R_2$ are together lower alkylene, a fused benzo ring or 1,3-dioxypropylene, $R_3$ and $R_4$ independent from one another are hydrogen, halogen, cyano, alkoxy having from 1 to 4 carbon atoms, sulfo, sulfonic acid ester, sulfonamido, mono- or dialkylsulfonamido and X is oxygen or sulfur.

2. Diamino-1,3,5-triazinylstilbene compounds as claimed in claim 1 wherein $R_1$ and $R_2$ independent from one another are hydrogen, fluorine, chlorine, phenyl, alkyl having from 1 to 9 carbon atoms, alkoxy having from 1 to 4 carbon atoms, carboxy, carbalkoxy having from 1 to 4 carbon atoms in the alkoxy moiety, cyano, sulfo, sulfonic acid ester, sulfonamido, mono- or dialkylsulfonamido or two vicinal radicals $R_1$ and $R_2$ are together lower alkylene or a fused benzo ring.

3. Diamino-1,3,5-triazinylstilbene compounds as claimed in claim 1 of the formula

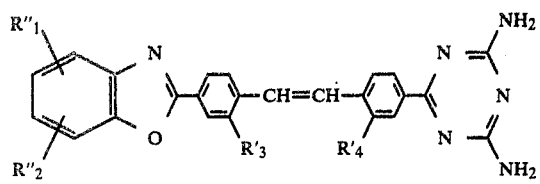

in which $R''_1$ and $R''_2$ independant from one another are hydrogen, fluorine or chlorine atoms, phenyl or alkyl having from 1 to 9 carbon atoms and $R'_3$ and $R'_4$ independant from one another are hydrogen, chlorine or cyano.

4. Diamino-1,3,5-triazinylstilbene compounds as claimed in claim 1 of the formula

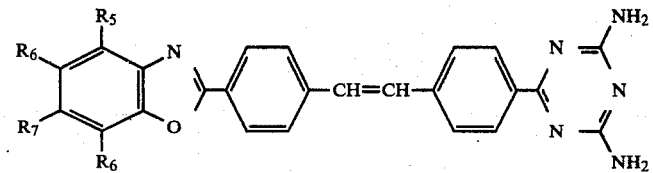

in which $R_5$, $R_6$, $R_7$ and $R_8$ each are hydrogen; $R_5$, $R_7$, $R_8$ each are hydogen and $R_6$ is chlorine, $C_{1-4}$ alkyl or phenyl; $R_5$ and $R_7$ each are hydrogen and $R_6$ and $R_8$ each are $C_{1-4}$ alkyl or $R_5$ and $R_8$ each are hydrogen and $R_6$ and $R_7$ each are $C_{1-4}$ alkyl.

* * * * *